(12) United States Patent
Funfschilling et al.

(10) Patent No.: US 7,112,673 B2
(45) Date of Patent: Sep. 26, 2006

(54) DIBENZO [B,F]AZEPINE INTERMEDIATES

(75) Inventors: Peter Funfschilling, Allschwil (CH); Daniel Kaufmann, Therwil (CH); Olivier Lohse, Rixheim (FR); Ulrich Beutler, Oberwil (CH); Werner Zaugg, Riehen (CH)

(73) Assignee: Novartis AG, Basel (CH)

( * ) Notice: Subject to any disclaimer, the term of this patent is extended or adjusted under 35 U.S.C. 154(b) by 235 days.

(21) Appl. No.: 10/182,980

(22) PCT Filed: Feb. 7, 2001

(86) PCT No.: PCT/EP01/01330

§ 371 (c)(1),
(2), (4) Date: Aug. 2, 2002

(87) PCT Pub. No.: WO01/56992

PCT Pub. Date: Aug. 9, 2001

(65) Prior Publication Data

US 2003/0032800 A1    Feb. 13, 2003

(30) Foreign Application Priority Data

Feb. 7, 2000 (GB) .................................. 0002740.9

(51) Int. Cl.
*C07D 223/22* (2006.01)
(52) U.S. Cl. ..................................................... 540/589
(58) Field of Classification Search ................ 540/589
See application file for complete search history.

(56) References Cited

U.S. PATENT DOCUMENTS 5,808,058 A * 9/1998 Milanese ..................... 540/588
6,048,856 A    4/2000 Jorgensen et al. ........... 514/217

FOREIGN PATENT DOCUMENTS

| WO | WO 96 21649 | 7/1996 |
|---|---|---|
| WO | WO 97/38978 | 10/1997 |
| WO | WO 01 03684 | 1/2001 |

OTHER PUBLICATIONS

MacNeil S.L. et al., "Directed ortho and Remote Metalation . . . Anthranilate Esters", Synlett Letters, pp. 419-421, (1998) XP-002171700.

* cited by examiner

*Primary Examiner*—Brenda Coleman
(74) *Attorney, Agent, or Firm*—Peter J. Waibel; Joseph J. Borovian; Edward J. Wilusz, Jr.

(57) ABSTRACT

The invention relates to new processes for the preparation of the pharmaceutical oxcarbazepine, as well as novel intermediates prepared by or used for said processes, and the preparation of said intermediates.

5 Claims, No Drawings

DIBENZO [B,F]AZEPINE INTERMEDIATES

The present invention relates to novel dibenzo [b,f] azepine derivatives and their preparation. The compounds of the invention are useful as intermediates for the preparation of pharmaceuticals.

More particularly the invention provides the compounds of formula I

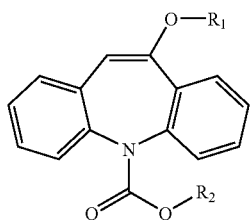

wherein $R_1$ is $(C_{1-4})$alkyl and $R_2$ is $(C_{1-4})$alkyl or phenyl.

The compounds of formula I are useful starting materials for the pharmaceutical oxcarbazepine (Trileptal®) of formula IV (see below), useful as anticonvulsant, e.g. in the treatment of epilepsy.

Oxcarbazepine can be prepared from the compounds of formula I for example according to the following reaction scheme:

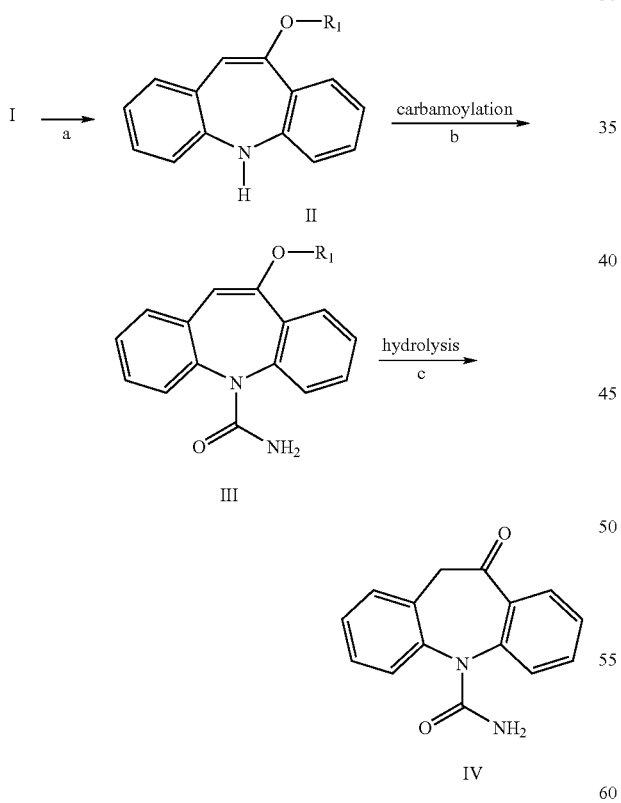

Reactions a, b and c may be carried out according to known procedures, for example as described in the Example, steps f to h.

In a further aspect the invention provides a process for the production of the compounds of formula I, whereby a compound of formula V

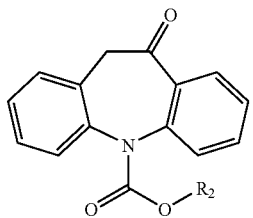

wherein $R_2$ is as defined above, is reacted with a compound of formula $R_1OH$ or $(R_1O)_3CH$, $R_1$ being as defined above.

The reaction may be effected in known manner, e.g. as described in the Example, steps d, d' and d".

The compounds of formula V have never been described in the literature and are also part of the present invention, as well as a process for their production.

According to the invention, the compounds of formula V can be prepared by ring closure of a compound of formula VI or VII

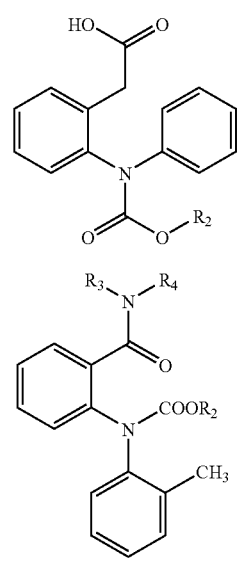

wherein $R_2$ is as defined above and $R_3$ and $R_4$, independently, are $(C_{1-4})$alkyl.

The ring closure of the compound of formula VI is suitably carried out under acidic conditions, e.g. as described in the Example, step c2. If the resulting compound of formula V is prepared for the preparation of a compound of formula I, it is preferably not isolated but reacted in situ into a compound of formula I, e.g. as described in the Example, step e.

It has surprisingly been found that this cyclisation leads to compounds of formula V and not to the 5-membered lactam of formula VIII

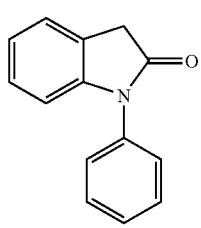

with cleavage of the —COOR$_2$, as would be expected from J. W. Schulenberg et al., J. Amer. Chem. Soc. 82, 2035 (1960) in view of the electron withdrawing character of the —COOR$_2$ group.

The ring closure of the compound of formula VII is suitably carried out under strongly alkaline conditions, e.g. as described in the Example, step c1.

The compounds of formula VI, as well as the compounds of formula VII wherein R$_2$ is not tert.-butyl when R$_3$ and R$_4$ are both isopropyl, are also novel and part of the present invention, as well as processes for their production.

According to the invention, the compounds of formula VI can be prepared by reaction of the compound of formula VIII under strong basic conditions with a compound of formula X—COOR$_2$, R$_2$ being as defined above and X being chlorine or methoxy. The reaction may be effected in conventional manner, e.g. as described in the Example, step a2.

Also according to the invention, the compounds of formula VII can be prepared by reaction of a compound of formula IX

IX

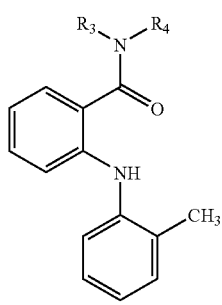

wherein R$_3$ and R$_4$ are as defined above, with a compound of formula Cl—COOR$_2$, R$_2$ being as defined above but not tert.-butyl when R$_3$ and R$_4$ are both isopropyl. The reaction may be effected in conventional manner, e.g. as described in the Example, step b.

The compounds of formula IX are also novel and part of the present invention. They may be prepared by reacting the compound of formula X

X

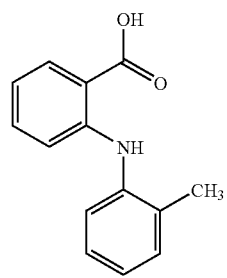

with a compound of formula R$_3$—NH—R$_4$, R$_3$ and R$_4$ being as defined above, in conventional manner, e.g. as described in the Example, step a1.

The starting materials of formulae VIII and X are known.

In still a further aspect the invention provides an improved process for the production of the compounds of formula III by carbamoylation of a compound of formula II. Carbamoylation of the compound of formula II wherein R is methyl is described in WO 96/21649. According to this disclosure, metal cyanates in the presence of mineral acids or relatively strong carboxylic acids and a solvent are used.

It has now surprisingly been found that this carbamoylation can also be achieved under mild conditions, using acetic acid. Presence of a strong acid and an additional solvent is not required. In view of the relatively low stability of the compounds of formula II, the absence of a strong acid is particularly advantageous. As a consequence the yield is significantly improved.

Accordingly the invention provides a process for the production of a compound of formula III by carbamoylation of a compound of formula II with a metal cyanate, whereby the reaction is effected using acetic acid, in the presence of a substantial excess of metal cyanate and in the absence of a further solvent.

The metal cyanate is preferably sodium or potassium cyanate. "Substantial excess" of metal cyanate means at least 0.2 equivalents, preferably 0.2 to 0.5 equivalents. Such excess is an essential condition for the reaction to take place with the improved yield as compared to the known carbamoylation process. The reaction may be effected for example as described in the Example, step g.

The following example illustrates the invention.

EXAMPLE a1) N,N-Dimethyl-2-o-tolylanino-benzamide 2-o-Tolylamino-benzoic acid (101 g, 0.444 mol) is suspended in toluene (800 mL) and heated to 58° C. A solution of thionyl chloride (57.6 g, 0.484 mol, 1,1 eq.) in toluene (100 mL) is added within 20 min. The mixture is slowly heated to 82° C. (1 hour) and concentrated in vacuum. Toluene (800 mL) is added to the evaporation residue and the solution is concentrated in vacuum. The crude acid chloride is dissolved in toluene (500 mL) and the solution is cooled down to 3° C. A solution of dimethylamine (61.3 mL of an aqueous 40% solution, 1.1 eq.), sodium hydroxide (77 g of a 30% aqueous solution, 1.3 eq.) and water (240 mL) is added in 45 min. The obtained suspension is stirred for 30 min. at 3° C. and then warmed to 30° C. The phases are separated and the aqueous phase is extracted with toluene (100 mL). The combined organic phases are washed twice with water (200 mL), evaporated to dryness and degassed in vacuum for 1 hour (30 mbar, 60° C.). The product is obtained as an oil that solidifies on standing (104.7 g, 93.5% yield). Eventually, the so obtained title compound can be recrystallized from cyclohexane.

b) (2-Dimethylcarbamoyl-phenyl)-o-tolyl-carbamic acid methyl ester

N,N-Dimethyl-2-o-tolylamino-benzamide (104.7 g, 0.412 mol, 1 eq.) is dissolved in toluene (800 mL) and cooled down to −8° C. A solution of n-Butyllithium in hexane (257 mL of a 1.6 M solution, 1 eq.) is added slowly in order to keep the temperature below 0° C. (1 hour). The orange suspension thus obtained is stirred for 30 min at −8° C. and methylchloroformiate (42.8 g, 1.1 eq.) is added in 30 min. The suspension is stirred for 1 hour at 5° C. before quenching with sodium bicarbonate (500 mL of a saturated aqueous solution). The phases are separated and the aqueous phase is extracted with toluene (200 mL). The combined organic phases are washed twice with water (200 mL), evaporated to dryness and degassed in vacuum for 1 hour (30 mbar, 60° C.). The crude compound (133.8 g) is dissolved in ethylacetate (240 mL) at 50° C. and hexane (990 mL) is added. The solution is allowed to cool down to 25° C. (30 min) whereby crystallization begins. The suspension is stirred for 1 hour at 25° C., cooled to 3° C. and stirred another 4 hours at this temperature. After filtration, the solid is washed with cold hexane and dried in vacuum for 16 hours (50° C., 50 mbar). The title compound is obtained as a slightly yellow solid (98.0 g, 70.5% global yield from 2-o-Tolylamino-benzoic acid).

c1) 10-Oxo-10,11-dihydro-dibenzo[b,f]azepine-5-carboxylic acid methyl ester

Diisopropylamine (11.66 g, 0.115 mol, 1.2 eq.) is dissolved in THF (150 mL) and the solution is cooled down to −10° C. A solution of n-Butyllithium in hexane (72 mL of a 1.6 M solution, 1.2 eq.) is added slowly in order to keep the temperature below 0° C. (40 min). A solution of (2-dimethylcarbamoyl-phenyl)-o-tolyl-carbamic acid methyl ester (30.2 g, 0.096 mol, 1 eq.) in THF (80 mL) is added in 45 min. to the obtained solution. The reaction mixture is stirred for 1 hour at −5° C. before quenching by addition of water (30 mL). The mixture is concentrated in vacuum and water (220 mL) and ethylacetate (220 mL) are added to the oily residue. The phases are stirred rapidly before letting them separate. The organic phase is washed with aqueous sulfuric acid (300 mL of 1-M solution) and twice with water (300 mL). The organic phase is evaporated to dryness and delivers 23.0 g (89.5% yield) of the title compound as an orange oil that solidifies on standing.

a2) [2-(Methoxycarbonyl-phenyl-amino)-phenyl]-acetic acid

A mixture of 1-phenyl-1,3-dihydro-indol-2-one (80 g, 382 mmol), sodium hydroxide (16.06 g, 402 mmol) and tetrahydrofuran (113 ml) is heated to reflux (67° C.) for 5 hours. The solution is diluted with another portion of tetrahydrofuran (169 ml) and cooled to −10° C. A 20% solution of butyllithium in cyclohexane (122.3 g, 382 mmol) is added at this temperature followed by dimethylcarbonate (51.7 g, 573 mmol). Afterwards, the solution is stirred at −10° C. for 2 hours. Concentrated hydrochloric acid (38 ml) and water (125 ml) are added and the organic solvents are distilled off at reduced pressure. After addition of toluene (345 ml) to the suspension, the pH of the water phase is adjusted to 1.5 using hydrochloric acid (34 ml). After phase separation at 75° C., the organic phase is washed with another portion of water (120 ml), concentrated at reduced pressure and allowed to crystallize at 0° C. to yield 81.2 g of pure title compound (75%).

d) 10-Methoxy-dibenzo[b,f]azepine-5-carboxylic acid methyl ester

Crude 10-Oxo-10,11-dihydro-dibenzo[b,f]azepine-5-carboxylic acid methyl ester (22.3 g, 0.083 mol, 1 eq.) is dissolved in methanol (112 mL) at 50° C. A catalytic amount of p-toluenesulfonic acid (0.445 mg) is added, followed by trimethyl orthoformate (11.5 mL, 1.25 eq.). The mixture is allowed to react for 5 hours before methanol is allowed to distill off. Fresh methanol is added continuously to replace the distillate. When 100 mL of methanol have been distilled, the mixture is allowed to cool down to 25° C. in 1 hour. The suspension is further cooled down to 3° C. in 20 minutes, stirred at this temperature for 1 hour and filtered. The solid is washed with cold methanol and dried in vacuum for 15 hours (50° C., 50 mbar). Pure title compound is obtained as a light yellow powder (18.02 g, 80.8% yield).

c2) 10-Oxo-10,11-dihydro-dibenzo[b,f]azepine-5-carboxylic acid methyl ester

A mixture of [2-(methoxycarbonyl-phenyl-amino)-phenyl]-acetic acid (16 g, 55.5 mmol) and polyphosphoric acid (29 g, 167 mmol in terms of $P_2O_5$) is heated to 100° C. for 4 hours. To the reaction mixture, water (41 ml) is added dropwise at 85–100° C. with stirring and cooling. At 65° C. toluene (41 ml) is added and the mixture is stirred for 30 min. The two phases are separated and washed. The organic phases are concentrated and allowed to crystallize at 0° C. to yield 12 g of pure title compound (80%).

d') 10-Methoxy-dibenzo[b,f]azepine-5-carboxylic acid methyl ester

A suspension of 10-oxo-10,11-dihydro-dibenzo[b,f]azepine-5-carboxylic acid methyl ester (15 g, 56 mmol) in methanol (75 ml) is heated to 60° C. and a catalytic amount of p-toluene sulfonic acid (0.213 g, 1.1 mmol) is added. After addition of trimethyl ortho-formate (6.25 g, 58.9 mmol) the solution is stirred at 60–70° C. for 4 hours. During this reaction the product precipitates as white crystals. The mixture is cooled to room temperature, filtered and dried to yield 15.5 g of pure title compound (98%).

d") 10-Ethoxy-dibenzo[b,f]azepine-5-carboxylic acid methyl ester

A suspension of 10-oxo-10,11-dihydro-dibenzo[b,f]azepine-5-carboxylic acid methyl ester (15 g, 56 mmol) in ethanol (75 ml) is heated to 60° C. and a catalytic amount of p-toluene sulfonic acid (0.213 g, 1.1 mmol) is added. After addition of triethyl ortho-formate (8.73 g, 58.9 mmol) the solution is stirred at 60–70° C. for 4 hours. During this reaction the product precipitates as white crystals. The mixture is cooled to room temperature, filtered and dried to yield 16.0 g of pure title compound (97%).

e) 10-Methoxy-dibenzo[b,f]azepine-5-carboxylic acid methyl ester

A mixture of [2-(methoxycarbonyl-phenyl-amino)-phenyl]-acetic acid (16 g, 55.5 mmol) and polyphosphoric acid (29 g, 167 mmol in terms of $P_2O_5$) is heated to 100° C. for 4 hours. To the reaction mixture, methanol (50 ml) is added dropwise at 65° C. with stirring. The resulting suspension is cooled to room temperature, filtered and washed with methanol (40 ml). The white crystals are dried to yield 12.2 g of pure title compound (80%).

f) 10-Methoxy-5H-dibenzo[b,f]azepine

A mixture of 10-methoxy-dibenzo[b,f]azepine-5-carboxylic acid methyl ester (19 g, 67.5 mmol), poly (ethylene glycol) 200 (20 ml) and sodium hydroxide solution 50% (13 ml, 246 mmol) is heated to 100° C. for 4 hours. Water (30 ml) is added and the suspension is cooled to 20° C. and filtered. The filter cake is washed with water and dried at 60° C./30 mbar to yield 147 g of pure title compound (98%).

g) 10-Methoxy-dibenzo[b,f]azepine-5-carboxylic acid amide

Acetic acid (150 mL) is added dropwise to a stirred mixture of 10-methoxy-5H-dibenzo[b,f]azepine (25.0 g, 112 mmol) and NaOCN (9.25 g, 142 mmol) under a nitrogen atmosphere at room temperature. After stirring for 7 hours the resulting yellow suspension of the title compound (>95% area of the compound by HPLC) is used for synthesis of 10-oxo-10,11-dihydro-dibenzo[b,f]azepine-5-carboxylic acid amide. The title compound can be isolated by adding 1N NaOH to a pH of ≧8 followed by extraction with toluene. Drying of the combined organic layers and concentration in vacuo yields the title compound as a light yellow solid (yield≧75%).

h) 10-Oxo-10,11-dihydro-dibenzo[b,f]azepine-5-carboxylic acid amide

To the acetic acid mixture obtained under g) is added water (12.5 mL, 694 mmol) and 100% $H_2SO_4$ (ca. 7.5 mL, 140 mmol) until a pH of $\leq 1$ is achieved. After stirring for 17 hours water is added (275 mL). The precipitated title compound is filtered and dried in vacuo (overall yield starting from 10-methoxy-5H-dibenzo[b,f]azepine $\geq 78\%$).

What is claimed is:

1. A process for the production of a compound of formula V

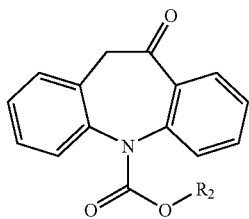

V wherein $R_2$ is $(C_{1-4})$alkyl or phenyl, which comprises the ring closure of a compound of formula VI

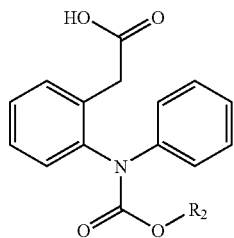

VI wherein $R_2$ is as defined above.

2. A process for the production of a compound of formula V according to claim 1, which comprises the ring closure of a compound of formula VII

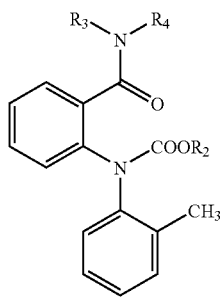

VII wherein $R_2$ is as defined in claim 1 and $R_3$ and $R_4$, independently, are $(C_{1-4})$alkyl.

3. A compound of formula V as defined in claim 1.

4. A compound of formula I

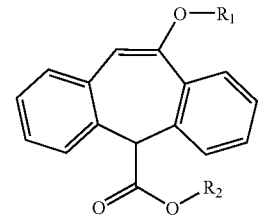

I wherein $R_1$ is $(C_{1-4})$alkyl and $R_2$ is as defined in claim 1.

5. A process for the production of a compound of formula I

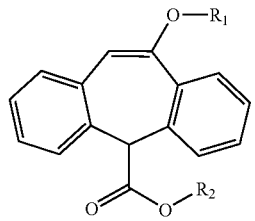

I wherein $R_1$ is $(C_{1-4})$alkyl and $R_2$ is $(C_{1-4})$alkyl or phenyl, which comprises reacting a compound of formula V as defined in claim 1 with a compound of formula $R_1OH$ or $(R_1O)_3CH$, wherein $R_1$ is as defined above.

* * * * *